(12) United States Patent
Galemmo et al.

(10) Patent No.: US 7,816,390 B2
(45) Date of Patent: *Oct. 19, 2010

(54) N-SUBSTITUTED TRICYCLIC 3-AMINOPYRAZOLES AS ANTI-MITOTIC TUBULIN POLYMERIZATION INHIBITORS

(75) Inventors: Robert A. Galemmo, Paoli, PA (US); Dana L. Johnson, Upper Black Eddy, PA (US); Umar S. M. Maharoof, North Wales, PA (US); Jay M. Mei, North Wales, PA (US); Robert W. Tuman, Chalfont, PA (US)

(73) Assignee: Janssen Pharmaceutica NV (BE)

( * ) Notice: Subject to any disclaimer, the term of this patent is extended or adjusted under 35 U.S.C. 154(b) by 135 days.

This patent is subject to a terminal disclaimer.

(21) Appl. No.: 12/021,535

(22) Filed: Jan. 29, 2008

(65) Prior Publication Data

US 2008/0227821 A1  Sep. 18, 2008

(51) Int. Cl.
*A61K 31/416* (2006.01)
*C07D 231/54* (2006.01)
(52) U.S. Cl. .................. 514/405; 548/359.1
(58) Field of Classification Search .............. 548/359.1; 514/405
See application file for complete search history.

(56) References Cited

U.S. PATENT DOCUMENTS

| 5,474,765 | A | 12/1995 | Thorpe |
| 5,762,918 | A | 6/1998 | Thorpe |
| 5,855,866 | A | 1/1999 | Thorpe et al. |
| 6,342,219 | B1 | 1/2002 | Thorpe et al. |
| 6,776,796 | B2 | 8/2004 | Falotico et al. |
| 7,196,110 | B2 * | 3/2007 | Ho et al. ............ 514/405 |
| 2002/0016625 | A1 | 2/2002 | Falotico et al. |

FOREIGN PATENT DOCUMENTS

| WO | WO 96/32907 | 10/1996 |
| WO | WO 03/097609 | 11/2003 |

OTHER PUBLICATIONS

Vippagunta et al., "Crystalline Solid", Advanced Drug Delivery Reviews 48 (2001) 3-26.*
Guillory (in Brittain ed.), Polymorphism, etc.,NY: Marcel Dekker, Inc., 1999, 1-2, 183-226.*
Gould, P., International J. Pharm. (1986), 33, pp. 201-217.
Berge et al., J. Pharm. Sci., (Jan. 1977), 66(1), pp. 1-19.
Libby P, "Vascular biology of atherosclerosis: overview and state of the art", Am J Cardiol (2003), 91(3A), pp. 3A-6A.

(Continued)

Primary Examiner—Patricia L Morris

(57) ABSTRACT

The invention is directed to compounds having the following structures:

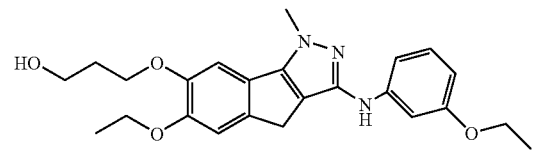

N-(3-ethoxyphenyl)-1,4-dihydro-6-ethoxy-7-(3-hydroxypropoxy)-1-methylindeno[1,2-c]pyrazole-3-amine;

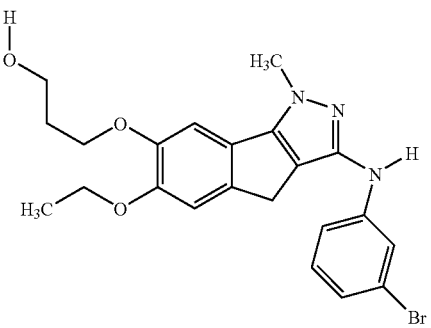

3-[3-(3-Bromo-phenylamino)-6-ethoxy-1-methyl-1,4-dihydro-indeno[1,2-c]pyrazol-7-yloxy]-propan-1-ol;
or

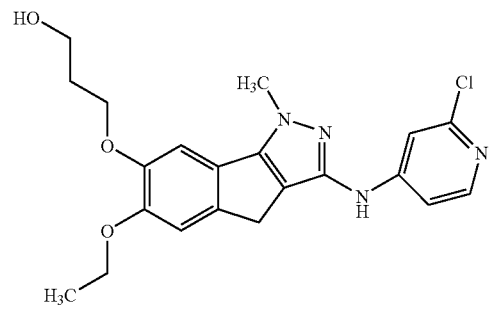

3-[3-(2-Chloro-pyridin-4-ylamino)-6-ethoxy-1-methyl-1,4-dihydro-indeno[1,2-c]pyrazol-7-yloxy]-propan-1-ol, and N-oxides, pharmaceutically acceptable salts, solvates, tautomers and stereochemical isomers thereof and the uses of such compounds as inhibitors of tubulin polymerization and for the treatment of solid tumors. The present invention is further directed to pharmaceutical compositions comprising the compounds of the present invention and to methods for treating conditions such as cancers and other cell proliferative disorders.

2 Claims, No Drawings

OTHER PUBLICATIONS

Helisch A, Schaper W., Arteriogenesis: the development and growth of collateral arteries. Microcirculation, (2003),10(1), pp. 83-97.

Holz FG et al.,"Pathogenesis of lesions in late age-related macular disease", Am J Ophthalmol. (2004), 137(3), pp. 504-510.

Schiele TM et. al.,"Vascular restenosis—striving for therapy." Expert Opin Pharmacother. (2004), 5(11), pp. 2221-2232.

Thannickal VJ et al., Idiopathic pulmonary fibrosis: emerging concepts on pharmacotherapy, Expert Opin Pharmacother. (2004), 5(8), pp. 1671-1686.

Cybulsky AV, "Growth factor pathways in proliferative glomerulonephritis", Curr Opin Nephrol Hypertens (2000), 9(3), pp. 217-223.

Harris RC et al, "Molecular basis of injury and progression in focal glomerulosclerosis" Nephron (1999), 82(4), pp. 289-299.

Woolf AS et al., "Evolving concepts in human renal dysplasia", J Am Soc Nephrol. (2004), 15(4), pp. 998-1007.

Grant MB et al.,"The role of growth factors in the pathogenesis of diabetic retinopathy", Expert Opin Investig Drugs (2004), 13(10), pp. 1275-1293.

Sweeney SE , Firestein GS, Rheumatoid arthritis: regulation of synovial inflammation, Int J Biochem Cell Biol. (2004), 36(3), pp. 372-378.

Simpson WG, The calcium channel blocker verapamil and cancer chemotherapy. Cell Calcium. (1985), 6(6), pp. 449-467.

Ricci A, et. al., "Neurotrophins and neurotrophin receptors in human pulmonary arteries." J Vasc Res. (2000), 37(5), pp. 355-363.

Kim H, et. al., "Paracrine and autocrine functions of brain-derived neurotrophic factor (BDNF) and nerve growth factor (NGF) in brain-derived endothelial cells", J Biol Chem. (2004), 279(32), pp. 33538-33546.

Douma S, et. al., "Suppression of anoikis and induction of metastasis by the neurotrophic receptor TrkB", Nature. (2004), 430(7003), pp. 1034-1040.

Arnon et al., "Monoclonal Antibodies for Immunotargeting of Drugs in Cancer Therapy", in Monoclonal Antibodies and Cancer Therapy, Reisfeld et al. (eds.), pp. 243-256 (Alan R. Liss, Inc. 1985).

Hellstrom et al., "Antibodies for Drug Delivery", in Controlled Drug Delivery (2nd Ed.), Robinson et al. (eds.), pp. 623-653 (Marcel Dekker, Inc. 1987).

Thorpe, "Antibody Carriers of Cytotoxic Agents in Cancer Therapy: A Review", in Monoclonal Antibodies '84: Biological and Clinical Applications, Pinchera et al. (eds.), pp. 475-506 (1985).

* cited by examiner ns 7,816,390 B2

N-SUBSTITUTED TRICYCLIC 3-AMINOPYRAZOLES AS ANTI-MITOTIC TUBULIN POLYMERIZATION INHIBITORS

FIELD OF THE INVENTION

The invention relates to novel compounds that function as potent, orally active inhibitors of tubulin polymerization, and pharmaceutical compositions and methods for treating solid tumors using said compounds.

BACKGROUND OF THE INVENTION

The present invention relates to N-substituted tricyclic 3-aminopyrazoles as inhibitors of tubulin polymerization and for use in treating solid tumors.

Malignant solid tumors are a leading cause of death throughout the world. There is a tremendous need for more efficacious treatments for all cancers. Currently, cancer is treated with a triad of approaches that include surgery, radiation and chemotherapy or, in most cases a combination of these treatment modalities. Existing chemotherapeutics kill tumor cells directly, but have relatively poor long-term efficacy in most cancers, are usually associated with debilitating side-effects (hematological, nausea, weight loss, neurotoxicity in the case of paclitaxel) and cannot be administered chronically. Advanced cancers are prone to develop resistance to chemotherapy due to their inherent genetic instability. For this reason, a good deal of current drug discovery research seeks to understand the mechanism(s) responsible for the development of multi-drug-resistant tumor phenotypes and to identify agents that are capable of over-coming this treatment-related resistance.

Particular interest has focused on discovery of novel agents that demonstrate activity in taxane and multi-drug resistant tumors and are capable of inhibiting angiogenesis by also targeting key processes involved in the process of tumor-induced angiogenesis.

Formation of new blood vessels within growing tumors appears to be an absolute requirement for tumor growth beyond a few millimeters and for the process of metastasis. Increased tumor vessel density compared to normal tissues has been demonstrated in many different tumors including colon, breast, lung and brain. In several studies, vessel density has correlated with disease progression and severity, and intratumor vascularity was an independent prognostic indicator.

The close interplay between angiogenesis and metastasis contributes to the poor prognosis of patients with highly angiogenic tumors. In the normal adult, vascular endothelium is quiescent, and active proliferation of endothelium for new blood vessels is limited to tumor tissues, wound healing or endometrial turnover.

Anti-angiogenic therapy has the potential to provide long-term suppression of tumor growth and metastasis without severe systemic toxic side effects or the development of resistance to therapy. Avastin (anti-VEGF), approved by the FDA in 2004, is effective at increasing the survival of stage III colorectal cancer patients, and has provided validation for the use of angiogenesis-targeted agents in cancer.

Microtubules are cytoskeleton protein polymers comprised of α-tubulin and β-tubulin polymers that are vital components of all cells and are critical for the maintenance of cell morphology. Microtubules form the basis of the mitotic apparatus in cells, and dynamically functioning microtubules are critical for normal cell division, as well as cell movement and attachment. Interference with microtubule dynamics prevents dividing cells from proceeding normally through the cell cycle and leads to G2/M cell cycle arrest and apoptosis.

Cancer cells acquire unlimited replicative potential and continually divide without going into quiescence or senescence. As a result of this uncontrolled growth, tumor cells are extremely dependent upon microtubule dynamics and, thus are susceptible to agents that interfere with microtubule dynamics either through stabilization of microtubule polymers or by inhibiting microtubule polymerization.

In addition, recent publications have demonstrated that proliferating endothelial cells involved in tumor-induced angiogenesis are also sensitive to the anti-mitotic action of tubulin modulators. These findings suggest that novel microtubule inhibitors, such as the compounds of the present invention, may impart dual anti-angiogenic and anti-tumor cell activities resulting in improved efficacy versus a broad range of tumor types.

Tubulin binding agents are one of the most successful classes of anti-cancer drugs in clinical use. However, the clinical usefulness of the current agents known in the art, such as paclitaxel (Taxol™), is limited by inherent resistance of many tumor types and by acquired resistance which develops in a high percentage of patients following multiple cycles of therapy. In addition, the side-effects of these agents are significant (e.g. myelosuppression, neurotoxicity) and can be dose-limiting either due to the compound itself or the vehicle required for intravenous administration. None of the currently approved agents are orally bioavailable.

Thus, identification of novel, orally active agents that target microtubules in proliferating tumor cells and in activated pro-angiogenic endothelial cells, together with demonstrated activities in multi-drug resistant tumor models and with improved side-effect profiles, remains among the most promising approaches for development of new anti-cancer drugs.

Currently, two main classes of anti-microtubule, anti-mitotic compounds are used clinically. Both classes differ from the compounds of the present invention by the mode of their interaction (binding) with microtubules.

The taxanes (paclitaxel and docetaxel) and epothilones (there are no approved epothilones) bind primarily to α-tubulin on microtubule polymers at the so-called taxane-binding site, stabilize existing microtubules and prevent depolymerization, thus forming stable, non-functional microtubules. In contrast, the Vinca alkaloids (vinblastine, vincristine and vinorelbine) bind to the tubulin polymer at the Vinca domain, inhibit the formation of new microtubules and thus inhibit formation of the necessary mitotic assembly required for cell division.

During the M-phase of the cell cycle, the dynamic microtubules that comprise the cell mitotic spindle are the target of most of the known tubulin-directed agents. Colchicine and the Vinca alkaloids bind to free β-tubulin and inhibit its polymerization into microtubules. Taxanes and epothilones bind to β-tubulin on the microtubules and prevent depolymerization, leading to uncontrolled microtubule formation. Both mechanisms lead to disruption of the mitotic spindle, metaphase arrest and subsequent apoptosis.

Although the ultimate mechanism of action of the various anti-mitotic agents is essentially the same (i.e. disruption of normal microtubule formation and dynamics), there are dramatic differences in the activity of the various agents against different cancer types. For example, the Vinca alkaloids, vinblastine, vincristine and vinorelbine, are generally more efficacious against hematological cancers and less effective versus solid tumors. In contrast, the taxanes, paclitaxel and docetaxel, are effective against ovarian, breast and lung solid tumors, but are relatively ineffective versus solid tumors of the colon, kidney and hematological cancers. A third class of anti-mitotic agents represented by colchicine, also inhibits tubulin polymerization by binding at the colchicine binding site, however none of these compounds have been used successfully in the oncology clinical arena due to extreme toxicity at efficacious doses and an extremely narrow therapeutic window. Accordingly, identification of orally active, small molecule anti-tubulin, anti-mitototic agents with less hematological and neuropathic toxicity and demonstrated activity in paclitaxel- and multi-drug (MDR)-resistant tumors, agents such as the compounds of the present invention, is critical to fulfilling the hereto unmet clinical need.

Systemic chemotherapy with cytotoxic agents has been the standard therapeutic approach to treating cancer known in the art. The majority of these chemotherapeutic compounds are microtubule inhibitors or DNA-damaging agents that are designed to kill rapidly dividing cells indiscriminately. In most cases, these agents are administered as a single bolus iv or short courses of therapy at the maximum tolerated dose (MTD). Because of adverse side-effects, this type of therapeutic approach requires fairly long dosing holidays (generally 2-3 weeks) between successive dosing cycles to allow recovery from the many toxicities associated with MTD-based therapy, including acute myelosuppression, loss of hair, GI-related side-effects, nausea and other adverse reactions. Supportive care is also frequently required to assist the patient's recovery from MTD-based therapy.

More recently, with the recognition that conventional cytotoxics also affect the endothelium of growing tumor vasculature at lower, relatively non-toxic doses, there has been a shift in the dosing paradigm toward using continuous, low non-MTD doses as an alternative approach to optimize the anti-angiogenic component of chemotherapy. This concept of administering low doses of chemotherapeutic drugs on a frequent or continuous schedule with no extended interruptions in therapy is known as 'metronomic chemotherapy'. In recent reports, the anti-angiogenic efficacy of metronomic dosing has been reported to yield significant clinical benefit without MTD-related toxicities. The compounds of the present invention present potent, orally active, colchicine-competitive inhibitors of tubulin polymerization. Accordingly, identification of orally active, small molecule anti-tubulin, anti-mitototic agents suitable for metronomic dosing, such as the compounds of the present invention, is critical to meeting the current clinical needs.

Secondary tumors are typically treated with aggressive chemotherapy or radiation. However, no approved therapies are currently directed toward blocking the deadly metastatic process. Potential intervention points in metastasis include tumor cell intravasation, extravasation, survival and proliferation within the target organ, and angiogenesis. Accordingly, the compounds of the present invention, however, by virtue of their dual anti-proliferative and anti-angiogenic activities, are useful for the prevention of metastases.

The published WO 2003097609 (2003) discloses similar tricyclic 3-aminopyrazoles. However, the instant application is directed to the compounds having the following structures:

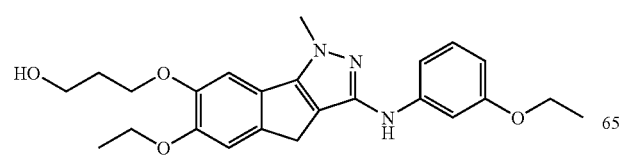

-continued

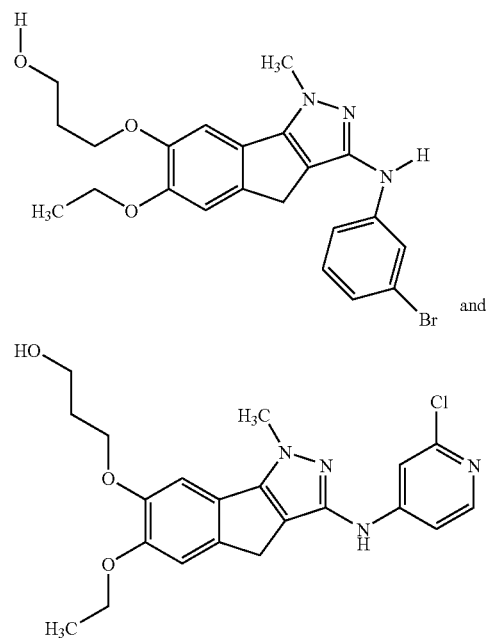

which exhibit surprisingly superior activity over the compounds in the reference.

SUMMARY OF THE INVENTION

Other features and advantages of the invention will be apparent from the following detailed description of the invention and from the claims.

DETAILED DESCRIPTION OF THE INVENTION

The compounds

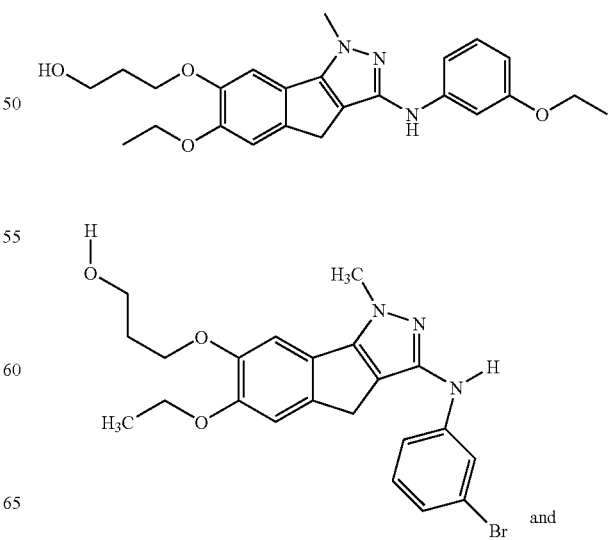

-continued

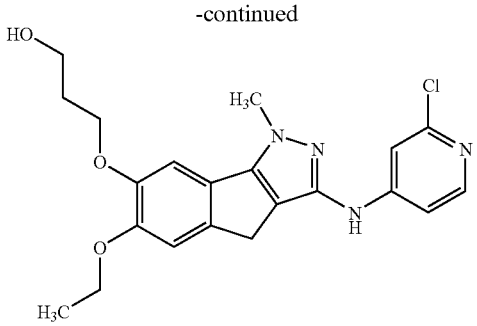

have demonstrated significant oral anti-angiogenic activity together with tumor cell anti-mitotic activity.

The compounds are novel, orally active, tubulin-directed anti-mitotic agents with demonstrated broad anti-tumor activity, together with significant in vivo anti-tumor activity versus paclitaxel-resistant, multi-drug-resistant tumor phenotypes and with an improved pre-clinical toxicity profile compared with paclitaxel. In addition, the compounds demonstrate significant anti-angiogenic activity both in vitro and in vivo, suggesting that the compound may provide a dual benefit by attacking both the tumor cell compartment and the capacity of the tumor to generate new vasculature to support further growth of the primary tumor as well as secondary micro-metastases. The observed anti-angiogenic activity at low efficacious doses also provides the potential opportunity to use the compound in a metronomic dosing paradigm. Furthermore, in vitro combination studies have clearly demonstrated synergistic activity with several agents including Tipifarnib (Zarnestra™) and cisplatin in NSCLC, suggesting the possibility of using it clinically in combination with these agents.

Compounds of the Invention

The present invention comprises the compounds:

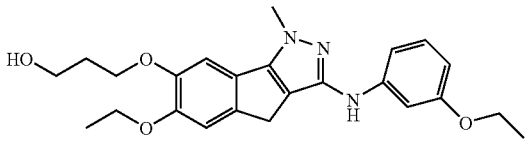

N-(3-ethoxyphenyl)-1,4-dihydro-6-ethoxy-7-(3-hydroxypropoxy)-1-methylindeno[1,2-c]pyrazole-3-amine;

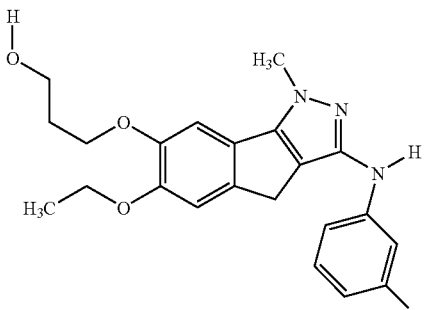

3-[3-(3-Bromo-phenylamino)-6-ethoxy-1-methyl-1,4-dihydro-indeno[1,2-c]pyrazol-7-yloxy]-propan-1-ol; and

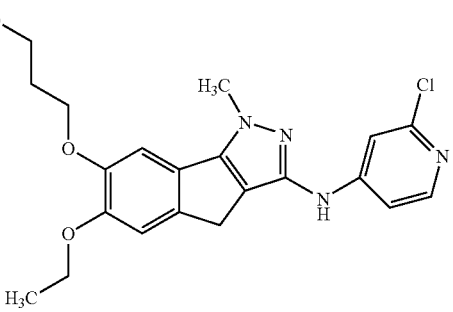

3-[3-(2-Chloro-pyridin-4-ylamino)-6-ethoxy-1-methyl-1, 4-dihydro-indeno[1,2-c]pyrazol-7-yloxy]-propan-1-ol; and N-oxides, pharmaceutically acceptable salts, solvates, tautomers and stereochemical isomers thereof.

Pharmaceutically Acceptable Salts

The compounds of the present invention may also be present in the form of pharmaceutically acceptable salts.

For use in medicines, the salts of the compounds of this invention refer to non-toxic "pharmaceutically acceptable salts." FDA approved pharmaceutically acceptable salt forms (Ref. International J. Pharm. 1986, 33, 201-217; J. Pharm. Sci., 1977, January, 66(1), p1) include pharmaceutically acceptable acidic/anionic or basic/cationic salts.

Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate and triethiodide. Organic or inorganic acids also include, and are not limited to, hydriodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid.

Pharmaceutically acceptable basic/cationic salts include, and are not limited to aluminum, 2-amino-2-hydroxymethylpropane-1,3-diol (also known as tris(hydroxymethyl)aminomethane, tromethane or "TRIS"), ammonia, benzathine, t-butylamine, calcium, calcium gluconate, calcium hydroxide, chloroprocaine, choline, choline bicarbonate, choline chloride, cyclohexylamine, diethanolamine, ethylenediamine, lithium, LiOMe, L-lysine, magnesium, meglumine, $NH_3$, $NH_4OH$, N-methyl-D-glucamine, piperidine, potassium, potassium-t-butoxide, potassium hydroxide (aqueous), procaine, quinine, sodium, sodium carbonate, sodium-2-ethylhexanoate (SEH), sodium hydroxide, triethanolamine (TEA) or zinc.

Prodrugs

The present invention includes within its scope prodrugs of the compounds of the invention. In general, such prodrugs will be functional derivatives of the compounds which are readily convertible in vivo into an active compound. Thus, in the methods of treatment of the present invention, the term "administering" shall encompass the means for treating, ameliorating or preventing a syndrome, disorder or disease described herein with a compound specifically disclosed or a compound, or prodrug thereof, which would obviously be included within the scope of the invention albeit not specifically disclosed for certain of the instant compounds. Conventional procedures for the selection and preparation of suitable prodrug derivatives are described in, for example, "*Design of Prodrugs*", ed. H. Bundgaard, Elsevier, 1985.

Stereochemical Isomers

One skilled in the art will recognize that the compounds may have one or more asymmetric carbon atoms in their structure. It is intended that the present invention include within its scope single enantiomer forms of the compounds, racemic mixtures, and mixtures of enantiomers in which an enantiomeric excess is present.

The term "single enantiomer" as used herein defines all the possible homochiral forms which the compounds and their N-oxides, addition salts, quaternary amines or physiologically functional derivatives may possess.

Stereochemically pure isomeric forms may be obtained by the application of art known principles. Diastereoisomers may be separated by physical separation methods such as fractional crystallization and chromatographic techniques, and enantiomers may be separated from each other by the selective crystallization of the diastereomeric salts with optically active acids or bases or by chiral chromatography. Pure stereoisomers may also be prepared synthetically from appropriate stereochemically pure starting materials, or by using stereoselective reactions.

Polymorphs and Solvates

Furthermore, compounds of the present invention may have one or more polymorph or amorphous crystalline forms and as such are intended to be included in the scope of the invention. In addition, some of the compounds may form solvates, for example, with water (i.e., hydrates) or common organic solvents, and such are also intended to be encompassed within the scope of this invention. As used herein, the term "solvate" means a physical association of one or more compounds of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include ethanolates, methanolates, and the like.

It is intended that the present invention include within its scope, solvates of the compounds of the present invention. Thus, in the methods of treatment of the present invention, the term "administering" shall encompass the means for treating, ameliorating or preventing a syndrome, disorder or disease described herein with a compound specifically disclosed or a compound, or solvate thereof, which would obviously be included within the scope of the invention albeit not specifically disclosed for certain of the instant compounds.

N-Oxides

The compounds may be converted to the corresponding N-oxide forms following art-known procedures for converting a trivalent nitrogen into its N-oxide form. Said N-oxidation reaction may generally be carried out by reacting the starting materials with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t-butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Tautomeric Forms

Some of the compounds may also exist in their tautomeric forms. Such forms although not explicitly indicated in the present application are intended to be included within the scope of the present invention.

Preparation of Compounds of the Present Invention

During any of the processes for preparation of the compounds of the present invention, it may be necessary and/or desirable to protect sensitive or reactive groups on any of the molecules concerned. This may be achieved by means of conventional protecting groups, which may be removed at a convenient subsequent stage using methods known in the art.

EXAMPLE OF PREPARATION OF THE REPRESENTATIVE COMPOUND

N-(3-ethoxyphenyl)-1,4-dihydro-6-ethoxy-7-(3-hydroxypropoxy)-1-methylindeno[1,2-c]pyrazole-3-amine The preparation of N-(3-ethoxyphenyl)-1,4-dihydro-6-ethoxy-7-(3-hydroxypropoxy)-1-methylindeno[1,2-c]pyrazole-3-amine on a multigram scale is accomplished in two stages: the first stage involves the preparation of a protected indanone intermediate, 3 (Scheme 1) and during the second stage, 3 is transformed to N-(3-ethoxyphenyl)-1,4-dihydro-6-ethoxy-7-(3-hydroxypropoxy)-1-methylindeno[1,2-c] pyrazole-3-amine (5, Scheme 2). A staged approach is convenient because the synthesis of intermediate 3 utilizes two chromatographies and the subsequent route from 3 to final product 5 requires one chromatographic separation to obtain pure material. The preparation of 5 can be improved by developing non-chromatographic purification methods throughout the synthesis.

The global demethylation of the commercially available starting material, 5,6-dimethoxyindanone is accomplished with an excess of $BBr_3$ in $CH_2Cl_2$ to give crude 1 in 100% yield (Scheme 1); this material requires no further purification to be used in the next step. Monoethylation of 1 to give 2 was achieved by stirring 1 with one equivalent of ethyliodide with excess potassium carbonate in DMF at ambient temperature for 18 h. The diethylation product is not observed but a substantial amount unreacted 1 remains after 18 h. In this case, pure 2 is obtained in 32% yield by rapid elution from a flash column followed by recrystallization from hexane: ethylacetate. The desired product 2 is soluble in $CHCl_3$, while the starting material impurity, 1, is not.

A Finkelstein modification of the Willamson Ether Synthesis is used to alkylate the free hydroxyl of 2 with 3-chloro-1-(tetrahydropyranyl)propanol. Following flash chromatography and trituration with pentane the product 3 is obtained in 87% yield as analytically pure material.

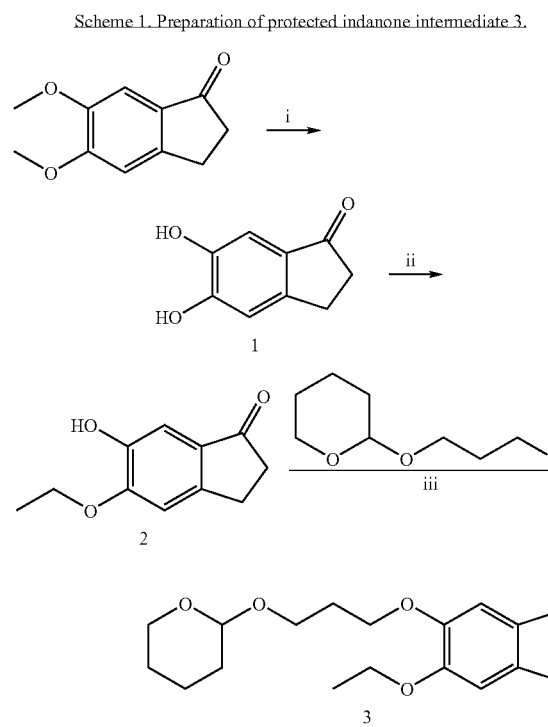

Scheme 1. Preparation of protected indanone intermediate 3.

Reagents and Conditions: i) BBr₃ (2.1 equivilents), CH₂Cl₂, -78° C., 4h; ii) K₂CO₃ (2.5 equivilents), C₂H₅I, DMF, RT, 18 h; iii) K₂CO₃ (2.5 equivilents), KI (2 equivilents), DMF, 65° C., 12 h, then RT, 8h.

The transformations required to prepare the compound N-(3-ethoxyphenyl)-1,4-dihydro-6-ethoxy-7-(3-hydroxypropoxy)-1-methylindeno[1,2-c]pyrazole-3-amine (5) from intermediate 3 are summarized in Scheme 2.

1-Ethoxy-3-isothiocyanatobenzene is not commercially available but can be prepared in one step by the reaction of 3-ethoxy aniline with 1,1'-thiocarbonyldi-2(1H)-pyridone in $CH_2Cl_2$. The enolate of indanone 3 is formed with lithium hexamethyldisilazane in toluene:tetrahydrofuran at −60° C. This solution is warmed to −30° C., quenched with 1-ethoxy-3-isothiocyanatobenzene, then warmed further to ambient temperature. After 4 h, the solvent is removed, the crude product is dissolved in ethanol and heated with methylhydrazine for 12 h. Flash chromatography of the resulting material gives a 53% yield of 4 followed by minor amounts of the 2-methyl, the N-demethylated and final product 5 from loss of the tertrahydropyranyl (THP) protecting group. The THP group is removed by transacetalation with p-toluene sulphonic acid in $CHCl_3$:methanol. Pure N-(3-ethoxyphenyl)-1,4-dihydro-6-ethoxy-7-(3-hydroxypropoxy)-1-methylindeno[1,2-c]pyrazole-3-amine (5) is obtained in 83% yield by precipitating the crude product from ethyl acetate:hexane.

Scheme 2. Preparation of N-(3-Ethoxyphenyl)-1,4-Dihydro-6-Ethoxy-7-(3-Hydroxypropoxy)-1-Methylindeno[1,2-C]Pyrazole-3-Amine, compound 5.

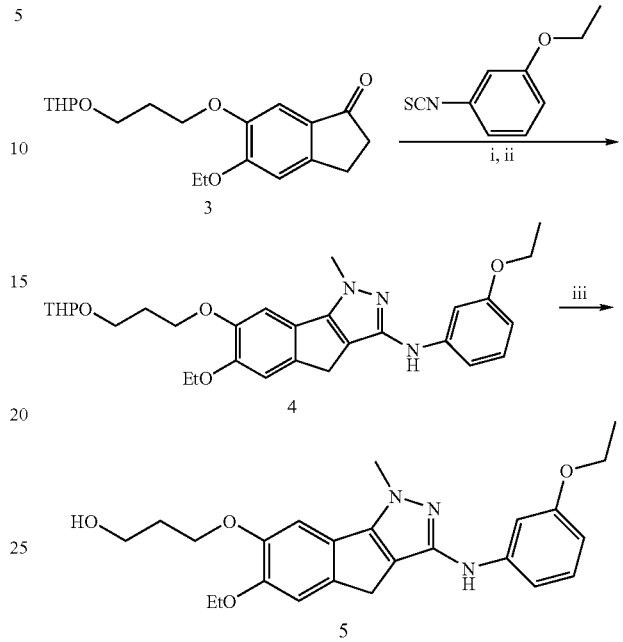

Reagents and Conditions: i) LiHMDSi (1.1 equivilents), THF, -60° C., 45 min; warm to -30° C., add isothiocyante (1.1 equivilents); warm to RT, 4h; ii) EtOH: dioxane (1:1), AcOH (2 equivilents), methylhydrazine (4 equivilents), 75° C., 4h; iii) CHCl₃ : MeOh (5:3), p-TsOH, 50° C., 4h.

The halo compounds are prepared in a similar manner using the appropriate halo-containing reagent.

Activity of the Compounds of this Invention

The novel chemical compounds described in this application, including the preferred compound N-(3-ethoxyphenyl)-1,4-dihydro-6-ethoxy-7-(3-hydroxypropoxy)-1-methylindeno[1,2-c]pyrazole-3-amine, have been shown to inhibit tubulin polymerization and de-stabilize microtubules in both tumor and proliferating endothelial cells. Initiation of the search for anti-mitotic tubulin inhibitors was based on the discovery and confirmation of inhibition of tubulin polymerization as the molecular target for the anti-proliferative mechanism of the dual mechanism tricyclic aminopyrazoles. The compounds exemplified in this patent were discovered as a distinct chemical subclass through chemical modification of the dual mechanism tricyclic aminopyrazole series to yield novel compounds that retain potent anti-tubulin, anti-proliferative activity but are devoid of the PDGFR kinase inhibitory activity characterized by compounds in the initial chemical series. In addition, rat and dog tolerability studies demonstrated that the dual mechanism compounds were associated with significant cardiotoxicity that was characterized by myocardial necrosis, preferential accumulation of compound in heart tissue relative to plasma and significant mortality. Subsequent follow-up studies in rats demonstrated that analogs with only a single predominant mechanism of action (i.e., either pure PDGFR kinase or pure anti-proliferative activity) did not exhibit histological evidence of drug-related cardiotoxicity at drug exposures up to 7× the efficacious AUC in the nude mouse and there was no evidence of drug accumulation in the hearts of rats subjected to repeated daily bid dosing for up to five days or in nude mice treated for up to 25 days with oral doses of up to 60 mg/kg bid.

The compounds exemplified in this patent inhibit tubulin polymerization with µM potency in the biochemical in vitro tubulin polymerization assay, potency similar to that described in the literature for nocadazole, colchicine and combretastatin using a tubulin biochemical assay. In in vitro cell-based proliferation assays, the µM potency in the biochemical assay translates to nM potent anti-proliferative activity versus a panel of human tumor cell lines. This dramatic shift in potency between the in vitro biochemical assay and the cell-based proliferation assay is well documented in the literature with reference tubulin inhibitors. The enhanced potency observed in cells is presumably due to the greater dynamic tubulin environment in proliferating cells that is more sensitive to disruption.

In Vitro Tubulin Polymerization Assay

Compounds were assayed in vitro for effects on tubulin polymerization using a commercially available assay kit from Cytoskeleton (CytoDYNAMIX Screen 03).

Methods: Briefly, this assay is based on the observation that light scattered by microtubules is proportional to the concentration of microtubule polymer. The standard polymerization reaction contains 100 µL volume of tubulin solution consisting of 3 mg/mL bovine tubulin in 80 mM PIPES pH 6.9, 0.5 mM EGTA, 2 mM $MgCl_2$, 1 mM GTP and 10% glycerol. The tubulin solution (100 µL/well) is added rapidly to wells of a 96-well plate containing duplicate aliquots (10 µL) of experimental compounds in DMSO to achieve a final well concentration of 1.0 and 10 µM in a preliminary screening assay. Control wells contain the same final concentration of DMSO (<0.5%). Following initiation of the polymerization reaction by incubation at 37° C., absorbance at 340 nm is measured every minute for 60 minutes using a SpectraMax plate reader. Under these assay conditions, control tubulin polymerization reaches a maximum $OD_{340}$ between 0.18 and 0.25 within 30 minutes of incubation followed by steady-state equilibrium. Under these conditions, approximately 85-90% of the tubulin in the reaction is polymerized. Paclitaxel (3 µM) and nocodazole (10 µM) or colchicines (2.5 µM) are routinely included as controls for tubulin stabilization and tubulin destabilization, respectively. Inhibition of tubulin polymerization by experimental compounds is calculated relative to the Vmax of the DMSO controls. A more detailed description of assay conditions and assay optimization can be found in the Assay Kit Instructions. The resulting polymerization curve (OD vs. Time in sec) is represented by three phases of microtubule polymerization, including nucleation (Phase I), microtubule growth (Phase II) and finally, steady-state equilibrium (Phase III). Compounds that interact (bind) with tubulin alter one or more of these characteristic phases of tubulin polymerization. For example, in this assay, the anti-mitotic agent paclitaxel, which stabilizes microtubules, shows an elimination of the nucleation phase and a dramatic enhancement of the Vmax of the growth phase at a concentration of 10 µM. In contrast, the microtubule de-stabilizer, nocodazole (10 µM) produces a significant decrease in the Vmax (OD/min) and a reduction in the final mass of tubulin polymer.

Results. The compound N-(3-ethoxyphenyl)-1,4-dihydro-6-ethoxy-7-(3-hydroxypropoxy)-1-methylindeno[1,2-c]pyrazole-3-amine produces a concentration-dependent inhibition of tubulin polymerization, with a calculated $IC_{50}$ of 2.4 µM. This inhibitory effect of N-(3-ethoxyphenyl)-1,4-dihydro-6-ethoxy-7-(3-hydroxypropoxy)-1-methylindeno[1,2-c]pyrazole-3-amine on tubulin polymerization is clearly distinct from paclitaxel, which produces stabilization of tubulin. The comparative activity of N-(3-ethoxyphenyl)-1,4-dihydro-6-ethoxy-7-(3-hydroxypropoxy)-1-methyl indeno[1,2-c]pyrazole-3-amine with other known tubulin inhibitors in the in vitro biochemical tubulin polymerization assay was determined as follows. The compound N-(3-ethoxyphenyl)-1,4-dihydro-6-ethoxy-7-(3-hydroxypropoxy)-1-methylindeno[1,2-c]pyrazole-3-amine exhibits an $IC_{50}$ of 2.4-3.7 µM compared to colchicine ($IC_{50}$=1.92 µM), nocodazole ($IC_{50}$=1.50 µM) and combretastatin ($IC_{50}$=1.31 µM). It should be pointed out that µM potency in this in vitro assay is well documented in the literature with a number of reference tubulin inhibitors and the dramatic shift in potency between the in vitro biochemical tubulin assay and the cell-based proliferation assay is a common and expected finding. The enhanced potency observed in cells with most tubulin inhibitors is presumably due to the greater dynamic tubulin environment in proliferating cells that is more sensitive to disruption.

Radiolabeled [$^3$H]-Colchicine Competition SPA Assay

To determine whether the compound N-(3-ethoxyphenyl)-1,4-dihydro-6-ethoxy-7-(3-hydroxypropoxy)-1-methylindeno[1,2-c]pyrazole-3-amine inhibits tubulin polymerization by interaction at the colchicine binding domain, the competitive binding activity of N-(3-ethoxyphenyl)-1,4-dihydro-6-ethoxy-7-(3-hydroxypropoxy)-1-methylindeno[1,2-c]pyrazole-3-amine was evaluated using a radiolabeled [$^3$H]-colchicine competition SPA assay. The compound competed with [$^3$H]-colchicine binding in a manner similar to unlabeled colchicine, compared to vinblastine which showed no significant competition. These results indicate that N-(3-ethoxyphenyl)-1,4-dihydro-6-ethoxy-7-(3-hydroxypropoxy)-1-methylindeno[1,2-c]pyrazole-3-amine binds to tubulin at the colchicine binding site which is different than the taxanes and the vinca alkaloids. The binding of this compound at the colchicine binding site was also demonstrated using another reagent assay, ThermoFluor®.

Inhibition of Tumor Cell Proliferation

The compound N-(3-ethoxyphenyl)-1,4-dihydro-6-ethoxy-7-(3-hydroxypropoxy)-1-methylindeno[1,2-c]pyrazole-3-amine was evaluated for direct effects on the growth of several human tumor cell lines derived from human cancers of varying origin (HeLa, cervical, H460 lung, LoVo colon, LnCAP and PC3 prostate lines, T47D breast, A375 melanoma, AsPC1 pancreatic and U87MG glioblastoma) and on the proliferation of normal human umbilical vein endothelial cells (HUVEC). Colchicine, nocodazole, doxorubicin and paclitaxel were evaluated as comparators.

Methods: Tumor cell anti-proliferative activity was assessed using standard in vitro cell proliferation assays in which the $IC_{50}$ for inhibition of cell proliferation by a compound was measured using $^{14}$C-thymidine incorporation into cellular DNA. Briefly, cells were plated into 96-well microplates and allowed to adhere overnight. Compound was added the next day and cells were incubated for an additional 24 hours. [$^{14}$C]-thymidine was allowed to incorporate into cellular DNA for 24 hours after which the plate was washed and counted in a scintillation counter.

Results: The comparative $IC_{50}$ values obtained for inhibition of cell proliferation for N-(3-ethoxyphenyl)-1,4-dihydro-6-ethoxy-7-(3-hydroxypropoxy)-1-methyl indeno[1,2-c]pyrazole-3-amine, colchicine, nocodazole, doxorubicin and paclitaxel are summarized as follows:

The compound N-(3-ethoxyphenyl)-1,4-dihydro-6-ethoxy-7-(3-hydroxypropoxy)-1-methylindeno[1,2-c]pyrazole-3-amine produced concentration-dependent inhibition of proliferation of a broad range of tumor cell types with nM potency. It demonstrated potent, concentration-dependent anti-proliferative activity versus 6 of 6 human tumor cell lines tested (AsPC-1, H460, PC3, T45D, A375, and LoVo), with $IC_{50}$ values in the low nM range (0.002-0.010 μM).

The compound N-(3-ethoxyphenyl)-1,4-dihydro-6-ethoxy-7-(3-hydroxypropoxy)-1-methylindeno[1,2-c]pyrazole-3-amine exhibited potency against these cell lines similar to that produced by the reference compounds. Depending on the cell line examined, the compound N-(3-ethoxyphenyl)-1,4-dihydro-6-ethoxy-7-(3-hydroxypropoxy)-1-methylindeno[1,2-c]pyrazole-3-amine was approximately 10-fold less potent compared to paclitaxel, which exhibited sub-nM potency versus H460 lung, T47D breast, PC3 prostate and LoVo colon lines. The test compound inhibited LSGS-stimulated HUVEC growth with an $IC_{50}$ of <0.010 μM, but was relatively less active versus confluent, non-proliferating HUVEC cells ($IC_{50}$>10 μM).

Methods of Treatment/Prevention

The term "prophylactically effective amount" refers to an amount of an active compound or pharmaceutical agent that inhibits or delays in a subject the onset of a disorder as being sought by a researcher, veterinarian, medical doctor or other clinician.

The term "therapeutically effective amount" as used herein, refers to an amount of active compound or pharmaceutical agent that elicits the biological or medicinal response in a subject that is being sought by a researcher, veterinarian, medical doctor or other clinician, which includes alleviation of the symptoms of the disease or disorder being treated.

Methods are known in the art for determining therapeutically and prophylactically effective doses for the instant pharmaceutical composition.

As used herein, the term "composition" is intended to encompass a product comprising the specified ingredients in the specified amounts, as well as any product which results, directly or indirectly, from combinations of the specified ingredients in the specified amounts.

The term "cell proliferative disorders" refers to unwanted cell proliferation of one or more subset of cells in a multicellular organism resulting in harm (i.e., discomfort or decreased life expectancy) to the multicellular organisms. Cell proliferative disorders can occur in different types of animals and humans. For example, as used herein "cell proliferative disorders" include neoplastic and other cell proliferative disorders.

As used herein, a "neoplastic disorder" refers to a tumor resulting from abnormal or uncontrolled cellular growth. Examples of neoplastic disorders include, but are not limited to, hematopoietic disorders such as, for instance, the myeloproliferative disorders, such as thrombocythemia, essential thrombocytosis (ET), agnogenic myeloid metaplasia, myelofibrosis (MF), myelofibrosis with myeloid metaplasia (MMM), chronic idiopathic myelofibrosis (IMF), and polycythemia vera (PV), the cytopenias, and pre-malignant myelodysplastic syndromes; cancers such as glioma cancers, lung cancers, breast cancers, colorectal cancers, prostate cancers, gastric cancers, esophageal cancers, colon cancers, pancreatic cancers, ovarian cancers, and hematoglogical malignancies, including myelodysplasia, multiple myeloma, leukemias and lymphomas. Examples of hematological malignancies include, for instance, leukemias, lymphomas (non-Hodgkin's lymphoma), Hodgkin's disease (also called Hodgkin's lymphoma), and myeloma—for instance, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocyctic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), and multiple myeloma, (MM).

Examples of other cell proliferative disorders, include but are not limited to, atherosclerosis (Libby P, 2003, "Vascular biology of atherosclerosis: overview and state of the art", Am J Cardiol 91 (3A):3A-6A) transplantation-induced vasculopathies (Helisch A, Schaper W. 2003, Arteriogenesis: the development and growth of collateral arteries. Microcirculation, 10(1):83-97), macular degeneration (Holz F G et al., 2004, "Pathogenesis of lesions in late age-related macular disease", Am J Opthalmol. 137(3):504-10), neointima hyperplasia and restenosis (Schiele T M et. al., 2004, "Vascular restenosis—striving for therapy." Expert Opin Pharmacother. 5(11):2221-32), pulmonary fibrosis (Thannickal V J et al., 2003, "Idiopathic pulmonary fibrosis: emerging concepts on pharmacotherapy, Expert Opin Pharmacother. 5(8):1671-86), glomerulonephritis (Cybulsky A V, 2000, "Growth factor pathways in proliferative glomerulonephritis", Curr Opin Nephrol Hypertens" 9(3):217-23), glomerulosclerosis (Harris R C et al, 1999, "Molecular basis of injury and progression in focal glomerulosclerosis" Nephron 82(4):289-99), renal dysplasia and kidney fibrosis (Woolf A S et al., 2004, "Evolving concepts in human renal dysplasia", J Am Soc Nephrol. 15(4):998-1007), diabetic retinopathy (Grant M B et al., 2004, "The role of growth factors in the pathogenesis of diabetic retinopathy", Expert Opin Investig Drugs 13(10): 1275-93) and rheumatoid arthritis (Sweeney S E, Firestein G S, 2004, Rheumatoid arthritis: regulation of synovial inflammation, Int J Biochem Cell Biol. 36(3):372-8).

As used herein, the terms "disorders related to TrkB", or "disorders related to the TrkB receptor", or "disorders related to the TrkB receptor tyrosine kinase" shall include diseases associated with or implicating TrkB activity, for example, the overactivity of TrkB, and conditions that accompany these diseases. The term "overactivity of TrkB" refers to either 1) TrkB expression in cells which normally do not express TrkB; 2) TrkB expression by cells which normally do not express TrkB; 3) increased TrkB expression leading to unwanted cell proliferation; or 4) increased TrkB expression leading to adhesion independent cell survival; 5) mutations leading to constitutive activation of TrkB. Examples of "disorders related to TrkB" include 1) disorders resulting from over stimulation of TrkB due to abnormally high amount of TrkB or mutations in TrkB, or 2) disorders resulting from abnormally high amount of TrkB activity due to abnormally high amount of TrkB or mutations in TrkB.

In an embodiment of the present invention, the compound of the present invention may be administered in combination with chemotherapy. As used herein, chemotherapy refers to a therapy involving a chemotherapeutic agent. A variety of chemotherapeutic agents may be used in the combined treatment methods disclosed herein. Chemotherapeutic agents contemplated as exemplary, include, but are not limited to: platinum compounds (e.g., cisplatin, carboplatin, oxaliplatin); taxane compounds (e.g., paclitaxcel, docetaxol); campotothecin compounds (irinotecan, topotecan); vinca alkaloids (e.g., vincristine, vinblastine, vinorelbine); anti-tumor nucleoside derivatives (e.g., 5-fluorouracil, leucovorin, gemcitabine, capecitabine) alkylating agents (e.g., cyclophosphamide, carmustine, lomustine, thiotepa); epipodophyllotoxins/podophyllotoxins (e.g. etoposide, teniposide); aromatase inhibitors (e.g., anastrozole, letrozole, exemestane); anti-estrogen compounds (e.g., tamoxifen, fulvestrant), antifolates (e.g., premetrexed disodium); hypomethylating agents (e.g., azacitidine); biologics (e.g., gemtuzamab, cetuximab, rituximab, pertuzumab, trastuzumab, bevacizumab, erlotinib); antibiotics/anthracyclines (e.g. idarubicin, actinomycin D, bleomycin, daunorubicin, doxorubicin, mitomycin C, dactinomycin, caminomycin, daunomycin); antimetabolites (e.g., aminopterin, clofarabine, cytosine arabinoside, methotrexate); tubulin-binding agents (e.g. combretastatin, colchicine, nocodazole); topoisomerase inhibitors (e.g., camptothecin). Further useful agents include verapamil, a calcium antagonist found to be useful in combination with antineoplastic agents to establish chemosensitivity in tumor cells resistant to accepted chemotherapeutic agents and to potentiate the efficacy of such compounds in drug-sensitive malignancies. See Simpson W G, The calcium channel blocker verapamil and cancer chemotherapy. Cell Calcium. 1985 December; 6(6): 449-67. Additionally, yet to emerge chemotherapeutic agents are contemplated as being useful in combination with the compound of the present invention.

In another embodiment of the present invention, the compound of the present invention may be administered in combination with radiation therapy. As used herein, "radiation therapy" refers to a therapy comprising exposing the subject in need thereof to radiation. Such therapy is known to those skilled in the art. The appropriate scheme of radiation therapy will be similar to those already employed in clinical therapies wherein the radiation therapy is used alone or in combination with other chemotherapeutics.

In another embodiment of the present invention, the compound of the present invention may be administered in combination with a gene therapy. As used herein, "gene therapy" refers to a therapy targeting on particular genes involved in tumor development. Possible gene therapy strategies include the restoration of defective cancer-inhibitory genes, cell transduction or transfection with antisense DNA corresponding to genes coding for growth factors and their receptors, RNA-based strategies such as ribozymes, RNA decoys, antisense messenger RNAs and small interfering RNA (siRNA) molecules and the so-called 'suicide genes'.

In other embodiments of this invention, the compound of the present invention may be administered in combination with an immunotherapy. As used herein, "immunotherapy" refers to a therapy targeting particular protein involved in tumor development via antibodies specific to such protein. For example, monoclonal antibodies against vascular endothelial growth factor have been used in treating cancers.

Where a second pharmaceutical is used in addition to a compound of the present invention, the two pharmaceuticals may be administered simultaneously (e.g. in separate or unitary compositions) sequentially in either order, at approximately the same time, or on separate dosing schedules. In the latter case, the two compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular chemotherapeutic agent being administered in conjunction with the compound of the present invention, their route of administration, the particular tumor being treated and the particular host being treated.

As will be understood by those of ordinary skill in the art, the appropriate doses of chemotherapeutic agents will be generally similar to or less than those already employed in clinical therapies wherein the chemotherapeutics are administered alone or in combination with other chemotherapeutics.

The optimum method and order of administration and the dosage amounts and regime can be readily determined by those skilled in the art using conventional methods and in view of the information set out herein.

By way of example only, platinum compounds are advantageously administered in a dosage of 1 to 500 mg per square meter ($mg/m^2$) of body surface area, for example 50 to 400 $mg/m^2$, particularly for cisplatin in a dosage of about 75 $mg/m^2$ and for carboplatin in about 300 $mg/m^2$ per course of treatment. Cisplatin is not absorbed orally and must therefore be delivered via injection intravenously, subcutaneously, intratumorally or intraperitoneally.

By way of example only, taxane compounds are advantageously administered in a dosage of 50 to 400 mg per square meter ($mg/m^2$) of body surface area, for example 75 to 250 $mg/m^2$, particularly for paclitaxel in a dosage of about 175 to 250 $mg/m^2$ and for docetaxel in about 75 to 150 $mg/m^2$ per course of treatment.

By way of example only, camptothecin compounds are advantageously administered in a dosage of 0.1 to 400 mg per square meter ($mg/m^2$) of body surface area, for example 1 to 300 $mg/m^2$, particularly for irinotecan in a dosage of about 100 to 350 $mg/m^2$ and for topotecan in about 1 to 2 $mg/m^2$ per course of treatment.

By way of example only, vinca alkaloids may be advantageously administered in a dosage of 2 to 30 mg per square meter ($mg/m^2$) of body surface area, particularly for vinblastine in a dosage of about 3 to 12 $mg/m^2$, for vincristine in a dosage of about 1 to 2 $mg/m^2$, and for vinorelbine in dosage of about 10 to 30 $mg/m^2$ per course of treatment.

By way of example only, anti-tumor nucleoside derivatives may be advantageously administered in a dosage of 200 to 2500 mg per square meter ($mg/m^2$) of body surface area, for example 700 to 1500 $mg/m^2$. 5-fluorouracil (5-FU) is commonly used via intravenous administration with doses ranging from 200 to 500 $mg/m^2$ (preferably from 3 to 15 mg/kg/day). Gemcitabine is advantageously administered in a dosage of about 800 to 1200 $mg/m^2$ and capecitabine is advantageously administered in about 1000 to 2500 $mg/m^2$ per course of treatment.

By way of example only, alkylating agents may be advantageously administered in a dosage of 100 to 500 mg per square meter ($mg/m^2$) of body surface area, for example 120 to 200 $mg/m^2$, particularly for cyclophosphamide in a dosage of about 100 to 500 $mg/m^2$, for chlorambucil in a dosage of about 0.1 to 0.2 mg/kg of body weight, for carmustine in a dosage of about 150 to 200 $mg/m^2$, and for lomustine in a dosage of about 100 to 150 $mg/m^2$ per course of treatment.

By way of example only, podophyllotoxin derivatives may be advantageously administered in a dosage of 30 to 300 mg per square meter (mg/m2) of body surface area, for example 50 to 250 $mg/m^2$, particularly for etoposide in a dosage of about 35 to 100 $mg/m^2$ and for teniposide in about 50 to 250 $mg/m^2$ per course of treatment.

By way of example only, anthracycline derivatives may be advantageously administered in a dosage of 10 to 75 mg per square meter ($mg/m^2$) of body surface area, for example 15 to 60 $mg/m^2$, particularly for doxorubicin in a dosage of about 40 to 75 $mg/m^2$, for daunorubicin in a dosage of about 25 to 45 $mg/m^2$, and for idarubicin in a dosage of about 10 to 15 $mg/m^2$ per course of treatment.

By way of example only, anti-estrogen compounds may be advantageously administered in a dosage of about 1 to 100 mg daily depending on the particular agent and the condition being treated. Tamoxifen is advantageously administered orally in a dosage of 5 to 50 mg, preferably 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

By way of example only, biologics may be advantageously administered in a dosage of about 1 to 5 mg per square meter ($mg/m^2$) of body surface area, or as known in the art, if different. For example, trastuzumab is advantageously administered in a dosage of 1 to 5 $mg/m^2$ particularly 2 to 4 $mg/m^2$ per course of treatment.

Dosages may be administered, for example once, twice or more per course of treatment, which may be repeated for example every 7, 14, 21 or 28 days.

The compounds of the present invention can be administered to a subject systemically, for example, intravenously, orally, subcutaneously, intramuscular, intradermal, or parenterally. The compounds of the present invention can also be administered to a subject locally. Non-limiting examples of local delivery systems include the use of intraluminal medical devices that include intravascular drug delivery catheters, wires, pharmacological stents and endoluminal paving. The compounds of the present invention can further be administered to a subject in combination with a targeting agent to achieve high local concentration of the compound at the target site. In addition, the compounds of the present invention may be formulated for fast-release or slow-release with the objective of maintaining the drugs or agents in contact with target tissues for a period ranging from hours to weeks.

The present invention also provides a pharmaceutical composition comprising the compounds in association with a pharmaceutically acceptable carrier. The pharmaceutical composition may contain between about 0.1 mg and 1000 mg, preferably about 100 to 500 mg, of the compound, and may be constituted into any form suitable for the mode of administration selected.

The phrases "pharmaceutically acceptable" refer to molecular entities and compositions that do not produce an adverse, allergic or other untoward reaction when administered to an animal, or a human, as appropriate. Veterinary uses are equally included within the invention and "pharmaceutically acceptable" formulations include formulations for both clinical and/or veterinary use.

Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

The pharmaceutical composition of the present invention also includes a pharmaceutical composition for slow release of a compound of the present invention. The composition includes a slow release carrier (typically, a polymeric carrier) and a compound of the present invention.

Slow release biodegradable carriers are well known in the art. These are materials that may form particles that capture therein an active compound(s) and slowly degrade/dissolve under a suitable environment (e.g., aqueous, acidic, basic, etc) and thereby degrade/dissolve in body fluids and release the active compound(s) therein. The particles are preferably nanoparticles (i.e., in the range of about 1 to 500 nm in diameter, preferably about 50-200 nm in diameter, and most preferably about 100 nm in diameter).

The present invention also provides methods to prepare the pharmaceutical compositions. The compounds as the active ingredients, are intimately admixed with a pharmaceutical carrier according to conventional pharmaceutical compounding techniques, which carrier may take a wide variety of forms depending on the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. In preparation for slow release, a slow release carrier, typically a polymeric carrier, and a compound of the present invention are first dissolved or dispersed in an organic solvent. The obtained organic solution is then added into an aqueous solution to obtain an oil-in-water-type emulsion. Preferably, the aqueous solution includes surface-active agent(s). Subsequently, the organic solvent is evaporated from the oil-in-water-type emulsion to obtain a colloidal suspension of particles containing the slow release carrier and the compound of the present invention.

The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, from about 0.01 mg to 200 mg/kg of body weight per day. Preferably, the range is from about 0.03 to about 100 mg/kg of body weight per day, most preferably, from about 0.05 to about 10 mg/kg of body weight per day. The compounds may be administered on a regimen of 1 to 5 times per day. The dosages, however, may be varied depending upon the requirement of the patients, the severity of the condition being treated and the compound being employed. The use of either daily administration or post-periodic dosing may be employed.

Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, acetyl alcohol and cellulose acetate.

The liquid forms in which the compounds may be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin. The liquid forms in suitably flavored suspending or dispersing agents may also include the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

Advantageously, the compounds may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The daily dosage of the products of the present invention may be varied over a wide range from 1 to 5000 mg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.01 mg/kg to about 200 mg/kg of body weight per day. Particularly, the range is from about 0.03 to about 15 mg/kg of body weight per day, and more particularly, from about 0.05 to about 10 mg/kg of body weight per day. The compound of the present invention may be administered on a regimen up to four or more times per day, preferably of 1 to 2 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

The compounds of the present invention can also be administered in the form of liposome delivery systems, such as small unilamellar vesicles, large unilamellar vesicles, and multilamellar vesicles. Liposomes can be formed from a variety of lipids, including but not limited to amphipathic lipids such as phosphatidylcholines, sphingomyelins, phosphatidylethanolamines, phophatidylcholines, cardiolipins, phosphatidylserines, phosphatidylglycerols, phosphatidic acids, phosphatidylinositols, diacyl trimethylammonium propanes, diacyl dimethylammonium propanes, and stearylamine, neutral lipids such as triglycerides, and combinations thereof. They may either contain cholesterol or may be cholesterol-free.

The compounds of the present invention can also be administered locally. Any delivery device, such as intravascular drug delivery catheters, wires, pharmacological stents and endoluminal paving, may be utilized. The delivery system for such a device may comprise a local infusion catheter that delivers the compound at a rate controlled by the administrator.

The present invention provides a drug delivery device comprising an intraluminal medical device, preferably a stent, and a therapeutic dosage of a compound of the invention.

The term "stent" refers to any device capable of being delivered by a catheter. A stent is routinely used to prevent vascular closure due to physical anomalies such as unwanted inward growth of vascular tissue due to surgical trauma. It often has a tubular, expanding lattice-type structure appropriate to be left inside the lumen of a duct to relieve an obstruction. The stent has a lumen wall-contacting surface and a lumen-exposed surface. The lumen-wall contacting surface is the outside surface of the tube and the lumen-exposed surface is the inner surface of the tube. The stent can be polymeric, metallic or polymeric and metallic, and it can optionally be biodegradable.

Commonly, stents are inserted into the lumen in a non-expanded form and are then expanded autonomously, or with the aid of a second device in situ. A typical method of expansion occurs through the use of a catheter-mounted angioplasty balloon which is inflated within the stenosed vessel or body passageway in order to shear and disrupt the obstructions associated with the wall components of the vessel and to obtain an enlarged lumen. Self-expanding stents as described in U.S. Pat. No. 6,776,796 (Falotico et al.) may also be utilized. The combination of a stent with drugs, agents or compounds which prevent inflammation and proliferation, may provide the most efficacious treatment for post-angioplastry restenosis.

Compounds of the invention can be incorporated into or affixed to the stent in a number of ways and in utilizing any number of biocompatible materials. In one exemplary embodiment, the compound is directly incorporated into a polymeric matrix, such as the polymer polypyrrole, and subsequently coated onto the outer surface of the stent. The compound elutes from the matrix by diffusion through the polymer. Stents and methods for coating drugs on stents are discussed in detail in the art. In another exemplary embodiment, the stent is first coated with as a base layer comprising a solution of the compound, ethylene-co-vinylacetate, and polybutylmethacrylate. Then, the stent is further coated with an outer layer comprising only polybutylmethacrylate. The outlayer acts as a diffusion barrier to prevent the compound from eluting too quickly and entering the surrounding tissues. The thickness of the outer layer or topcoat determines the rate at which the compound elutes from the matrix. Stents and methods for coating are discussed in detail in WIPO publication WO9632907, U.S. Publication No. 2002/0016625 and references disclosed therein.

The solution of the compound of the invention and the biocompatible materials/polymers may be incorporated into or onto a stent in a number of ways. For example, the solution may be sprayed onto the stent or the stent may be dipped into the solution. In a preferred embodiment, the solution is sprayed onto the stent and then allowed to dry. In another exemplary embodiment, the solution may be electrically charged to one polarity and the stent electrically changed to the opposite polarity. In this manner, the solution and stent will be attracted to one another. In using this type of spraying process, waste may be reduced and more control over the thickness of the coat may be achieved. Compound is preferably only affixed to the outer surface of the stent which makes contact with one tissue. However, for some compounds, the entire stent may be coated. The combination of the dose of compound applied to the stent and the polymer coating that controls the release of the drug is important in the effectiveness of the drug. The compound preferably remains on the stent for at least three days up to approximately six months and more, preferably between seven and thirty days.

Any number of non-erodible biocompatible polymers may be utilized in conjunction with the compound of the invention. It is important to note that different polymers may be utilized for different stents. For example, the above-described ethylene-co-vinylacetate and polybutylmethacrylate matrix works well with stainless steel stents. Other polymers may be utilized more effectively with stents formed from other materials, including materials that exhibit superelastic properties such as alloys of nickel and titanium.

Restenosis is responsible for a significant morbidity and mortality following coronary angioplasty. Restenosis occurs through a combination of four processes including elastic recoil, thrombus formation, intima hyperplasia and extracellular matrix remodeling. Several growth factors have been recently identified to play a part in these processes leading to restenosis (see, Schiele T M et. al., 2004, "Vascular restenosis—striving for therapy." Expert Opin Pharmacother. 5(11): 2221-32.). Of note, TrkB ligands BDNF and neurotrophins as well as TrkB are expressed by vascular smooth muscle cells and endothelial cells (see, Ricci A, et. al. 2003", Neurotrophins and neurotrophin receptors in human pulmonary arteries." J Vasc Res. 37(5):355-63; see also, Kim H, et. al., 2004 "Paracrine and autocrine functions of brain-derived neurotrophic factor (BDNF) and nerve growth factor (NGF) in brain-derived endothelial cells", J Biol. Chem. 279(32):33538-46). Additionally, TrkB may play a role in peripheral angiogenesis and intima hyperplasia because of its ability to prevent anoikis and prolong cell survival (see, Douma S, et. al., 2004, "Suppression of anoikis and induction of metastasis by the neurotrophic receptor TrkB", Nature. 430(7003):1034-9.). Therefore, inhibition of TrkB during and following coronary angioplasty using a coated stent presents a viable therapeutic strategy.

Accordingly, the present invention provides a method for the treatment of disorders related to TrkB, including restenosis, intimal hyperplasia or inflammation, in blood vessel walls, in a subject comprising administering to the subject a compound of the invention in a therapeutically effective amounts by the controlled delivery, by release from an intraluminal medical device, such as a stent, of the compound of the invention.

Methods for introducing a stent into a lumen of a body are well known and the compound-coated stents of this invention are preferably introduced using a catheter. As will be appreciated by those of ordinary skill in the art, methods will vary slightly based on the location of stent implantation. For coronary stent implantation, the balloon catheter bearing the stent is inserted into the coronary artery and the stent is positioned at the desired site. The balloon is inflated, expanding the stent. As the stent expands, the stent contacts the lumen wall. Once the stent is positioned, the balloon is deflated and removed. The stent remains in place with the lumen-contacting surface bearing the compound directly contacting the lumen wall surface. Stent implantation may be accompanied by anticoagulation therapy as needed.

Optimum conditions for delivery of the compounds for use in the stent of the invention may vary with the different local delivery systems used, as well as the properties and concentrations of the compounds used. Conditions that may be optimized include, for example, the concentrations of the compounds, the delivery volume, the delivery rate, the depth of penetration of the vessel wall, the proximal inflation pressure, the amount and size of perforations and the fit of the drug delivery catheter balloon. Conditions may be optimized for inhibition of smooth muscle cell proliferation at the site of injury such that significant arterial blockage due to restenosis does not occur, as measured, for example, by the proliferative ability of the smooth muscle cells, or by changes in the vascular resistance or lumen diameter. Optimum conditions can be determined based on data from animal model studies using routine computational methods.

Another alternative method for administering compounds of this invention may be by conjugating the compound to a targeting agent which directs the conjugate to its intended site of action, i.e., to vascular endothelial cells, or to tumor cells. Both antibody and non-antibody targeting agents may be used. Because of the specific interaction between the targeting agent and its corresponding binding partner, a compound of the present invention can be administered with high local concentrations at or near a target site and thus treats the disorder at the target site more effectively.

The antibody targeting agents include antibodies or antigen-binding fragments thereof, that bind to a targetable or accessible component of a tumor cell, tumor vasculature, or tumor stroma. The "targetable or accessible component" of a tumor cell, tumor vasculature or tumor stroma, is preferably a surface-expressed, surface-accessible or surface-localized component. The antibody targeting agents also include antibodies or antigen-binding fragments thereof, that bind to an intracellular component that is released from a necrotic tumor cell. Preferably such antibodies are monoclonal antibodies, or antigen-binding fragments thereof, that bind to insoluble intracellular antigen(s) present in cells that may be induced to be permeable, or in cell ghosts of substantially all neoplastic and normal cells, but are not present or accessible on the exterior of normal living cells of a mammal.

As used herein, the term "antibody" is intended to refer broadly to any immunologic binding agent such as IgG, IgM, IgA, IgE, F(ab')2, a univalent fragment such as Fab', Fab, Dab, as well as engineered antibodies such as recombinant antibodies, humanized antibodies, bispecific antibodies, and the like. The antibody can be either the polyclonal or the monoclonal, although the monoclonal is preferred. There is a very broad array of antibodies known in the art that have immunological specificity for the cell surface of virtually any solid tumor type (see, Summary Table on monoclonal antibodies for solid tumors in U.S. Pat. No. 5,855,866 to Thorpe et al). Methods are known to those skilled in the art to produce and isolate antibodies against tumor (see, U.S. Pat. No. 5,855,866 to Thorpe et al., and U.S. Pat. No. 6,342,219 to Thorpe et al.).

Techniques for conjugating therapeutic moiety to antibodies are well known. (See, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985)). Similar techniques can also be applied to attach compounds of the invention to non-antibody targeting agents. Those skilled in the art will know, or be able to determine, methods of forming conjugates with non-antibody targeting agents, such as small molecules, oligopeptides, polysaccharides, or other polyanionic compounds.

Although any linking moiety that is reasonably stable in blood, can be used to link the compounds of the present invention to the targeting agent, biologically-releasable bonds and/or selectively cleavable spacers or linkers are preferred. "Biologically-releasable bonds" and "selectively cleavable spacers or linkers" still have reasonable stability in the circulation, but are releasable, cleavable or hydrolyzable only or preferentially under certain conditions, i.e., within a certain environment, or in contact with a particular agent. Such bonds include, for example, disulfide and trisulfide bonds and acid-labile bonds, as described in U.S. Pat. Nos. 5,474,765 and 5,762,918 and enzyme-sensitive bonds, including peptide bonds, esters, amides, phosphodiesters and glycosides as described in U.S. Pat. Nos. 5,474,765 and 5,762,918. Such selective-release design features facilitate sustained release of the compounds from the conjugates at the intended target site.

The present invention provides a pharmaceutical composition comprising an effective amount of a compound of the present invention conjugated to a targeting agent and a pharmaceutically acceptable carrier.

When proteins such as antibodies or growth factors, or polysaccharides are used as targeting agents, they are preferably administered in the form of injectable compositions. The injectable antibody solution will be administered into a vein, artery or into the spinal fluid over the course of from 2 minutes to about 45 minutes, preferably from 10 to 20 minutes. In certain cases, intradermal and intracavitary administration are advantageous for tumors restricted to areas close to particular regions of the skin and/or to particular body cavities. In addition, intrathecal administrations may be used for tumors located in the brain.

Therapeutically effective dose of the compound of the present invention conjugated to a targeting agent depends on the individual, the disease type, the disease state, the method of administration and other clinical variables. The effective dosages are readily determinable using data from an animal model. Experimental animals bearing solid tumors are frequently used to optimize appropriate therapeutic doses prior to translating to a clinical environment. Such models are known to be very reliable in predicting effective anti-cancer strategies. For example, mice bearing solid tumors, are widely used in pre-clinical testing to determine working ranges of therapeutic agents that give beneficial anti-tumor effects with minimal toxicity.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. The compounds having the following structures:

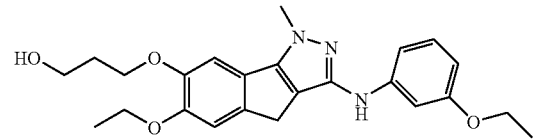

N-(3-ethoxyphenyl)-1,4-dihydro-6-ethoxy-7-(3-hydroxypropoxy)-1-methylindeno[1,2-c]pyrazole-3-amine; or

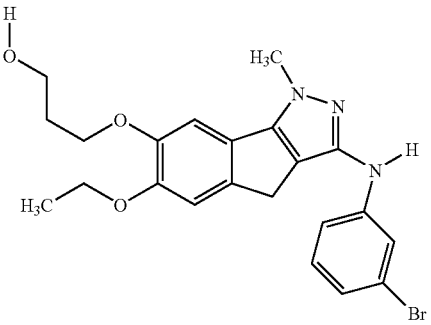

3-[3-(3-Bromo-phenylamino)-6-ethoxy-1-methyl-1,4-dihydro-indeno[1,2-c]pyrazol-7-yloxy]-propan-1-ol;

and N-oxide, pharmaceutically acceptable salt, tautomer and stereochemical isomer thereof.

2. A pharmaceutical composition comprising the compound of claim 1 and a pharmaceutically acceptable carrier.

* * * * *